United States Patent [19]

Erdmann et al.

[11] Patent Number: 5,112,432
[45] Date of Patent: * May 12, 1992

[54] ORGANOMETALLIC COMPOUNDS

[75] Inventors: Dietrich Erdmann, Mühltal; Max E. Van Ghemen; Ludwig Pohl, both of Darmstadt; Herbert Schumann, Berlin; Uwe Hartmann, Berlin; Wilfried Wassermann, Berlin; Meino Heyen; Holger Jürgensen, both of Aachen, all of Fed. Rep. of Germany

[73] Assignee: Merck Patent Gesellschaft mit Beschrankter Haftung, Darmstadt, Fed. Rep. of Germany

[ * ] Notice: The portion of the term of this patent subsequent to Nov. 14, 2006 has been disclaimed.

[21] Appl. No.: 389,197

[22] Filed: Aug. 3, 1989

Related U.S. Application Data

[63] Continuation-in-part of Ser. No. 96,583, Sep. 15, 1987, Pat. No. 4,880,492.

[30] Foreign Application Priority Data

Sep. 16, 1986 [DE] Fed. Rep. of Germany ....... 3631469

[51] Int. Cl.$^5$ .................. C23C 16/30; C30B 25/02; C30B 29/40

[52] U.S. Cl. .................. 156/610; 156/613; 156/DIG. 61; 156/DIG. 70; 427/252; 427/255.2

[58] Field of Search ............ 156/61.0, 613, DIG. 61, 156/DIG. 70; 427/252, 255.2; 556/70, 30

[56] References Cited

U.S. PATENT DOCUMENTS

| | | | |
|---|---|---|---|
| 4,250,205 | 2/1981 | Constant et al. | 427/248.1 |
| 4,509,997 | 4/1985 | Cockayne | 156/613 |
| 4,594,264 | 6/1986 | Jensen | 427/54.1 |
| 4,734,387 | 5/1988 | Nelson et al. | 156/613 |
| 4,734,514 | 3/1988 | Melas et al. | 568/17 |
| 4,792,467 | 12/1988 | Melas et al. | 427/255 |
| 4,833,103 | 5/1989 | Agostinelli et al. | 427/226 |
| 4,879,397 | 11/1989 | Theopold et al. | 556/11 |
| 4,880,492 | 11/1989 | Erdmann et al. | 156/610 |
| 4,904,616 | 2/1990 | Bohling et al. | 148/DIG. 110 |
| 4,975,299 | 12/1990 | Mir et al. | 427/255.2 |

Primary Examiner—Gary P. Straub
Attorney, Agent, or Firm—Millen, White & Zelano

[57] ABSTRACT

In a process for the production of thin films and epitaxial layers by gas-phase deposition, intramolecularly stabilized organometallic compounds are employed as a source of metal.

7 Claims, No Drawings

ORGANOMETALLIC COMPOUNDS

CROSS-REFERENCE TO RELATED APPLICATION

This application is a continuation-in-part of application Ser. No. 07/096,583, filed Sep. 15, 1987 now U.S. Pat. No. 4,880,492.

BACKGROUND OF THE INVENTION

The invention relates to the use of organometallic compounds containing aluminum, gallium or indium as metals for the production of thin films or epitaxial layers by gas-phase deposition.

The deposition of such layers consisting either of pure elements of group III or of combinations with other elements, such as, for example, gallium arsenide, indium phosphide or gallium phosphide, can be used to produce electronic and optoelectronic switching elements, compound semiconductors and lasers. Such layers are deposited from the gas phase.

The properties of such films depend on the deposition conditions and on the chemical composition of the deposited film.

All the known methods, such as the metal-organic chemical vapor deposition method (MOCVD), the photo-metal-organic vapor phase method (photo-MOVP) in which the substances are decomposed by UV radiation, the laser chemical vapor deposition (laser CVD) method or the metal-organic magnetron sputtering method (MOMS) are suitable for the deposition from the gas phase. The advantages over other methods are a controllable layer growth, a precise doping control, and also simple handling and ease of production owing to the normal or low-pressure conditions.

In the MOCVD method, organometallic compounds are used which decompose at a temperature below 1100° C. with the deposition of the metal. Typical pieces of equipment which are at present used for MOCVD consist of a "bubbler" with a feed for the organometallic components, a reaction chamber which contains the substrate to be coated, and also a source for a carrier gas which should be inert with respect to the organometallic component. The "bubbler" is kept at a constant, relatively low temperature which is preferably above the melting point of the organometallic compound but far below the decomposition temperature. The reaction or decomposition chamber preferably has a very much higher temperature, which is below 1100° C., at which the organometallic compound completely decomposes and the metal is deposited. The organometallic compound is converted to the vapor state by the carrier gas and is channelled into the decomposition chamber with the carrier gas. The mass flowrate of the vapor can readily be controlled and, consequently, a controlled growth of the thin layers is also possible.

Hitherto metal alkyls such as, for example, trimethylgallium, trimethylaluminum or trimethylindium have chiefly been used for gas-phase deposition. However, these compounds are extremely sensitive to air, spontaneously inflammable and, in some cases, unstable even at room temperature. Costly precautionary measures are therefore necessary for the production, transport, storage and use of said compounds. A few, somewhat more stable adducts of the metal alkyls with lewis bases, such as, for example, trimethylamine and triphenylphosphine, are known (for example, described in GB 2,123,422, EP-A-108,469 or EP-A-176,537), but these are only of limited suitability for gas-phase deposition because of the low vapor pressure.

SUMMARY OF THE INVENTION

An object of the present invention is to provide metal alkyl compounds which are simple to handle, are stable at room temperature and can be decomposed from the gas phase, i.e. are suitable for the various methods of gas-phase deposition.

Upon further study of the specification and appended claims, further objects and advantages of this invention will become apparent to those skilled in the art.

It has now been found that organometallic compounds of aluminum, gallium and indium which are intramolecularly stabilized are outstandingly suitable for gas-phase deposition.

Intramolecularly stabilized compounds of this type containing aluminum as metal atom are described, for example, in U.S. Pat. No. 3,154,528, specifically for use as catalyst systems in polymerization reactions. Furthermore, in Organometallics 1982, i, 1492-1495, an indium derivative, 2-(dimethylaminomethyl)phenyl-dimethylindium, is described which was used for structural investigations by means of nuclear resonance spectroscopy.

The objects of the invention have therefore been achieved by the use of organometallic compounds of formula I

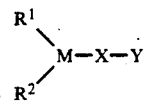

wherein
 M denotes aluminum, indium, or gallium,
 X denotes —(CHR$^5$)$_n$—where n=2, 3, 4 or 5, —2—C$_6$H$_4$—(CH$_2$)$_m$—, —(CH$_2$)$_m$—2—C$_6$H$_4$—, —2—C$_6$H$_{10}$—(CH$_2$)$_m$—, —(CH$_2$)$_m$—2—C$_6$H$_{10}$— where m=1 or 2,
 R$^5$ in each case denotes H or an alkyl group containing 1-4 carbon atoms,
 Y denotes a 5- or 6-membered heterocyclic ring, the heteroatom(s) originating from group 5A, or —NR$^3$R$^4$, —PR$^3$R$^4$, —AsR$^3$R$^4$, or —SbR$^3$R$^4$, and
 R$^1$, R$^2$, R$^3$ and R$^4$ in each case denote, independently of each other, H, a straight-chain or branched alkyl group containing 1-8 carbon atoms, which may be partially or completely fluorinated, a cycloalkyl, alkenyl or cycloalkenyl group containing in each case 3-8 carbon atoms or an unsubstituted or substituted phenyl group, for gas-phase deposition and also a method for producing thin films or epitaxial layers by gas-phase deposition of the metal from organometallic compounds in which the compounds of the formula I are used as organometallic compounds. Furthermore, a subject of the invention is that, in the novel method for preparing compounded semiconductors, one or more compounds of arsenic, antimony or phosphorus which are gaseous under the reaction conditions employed, are supplied during the deposition process.

In formula I M preferably denotes indium or gallium. Preferably, X denotes —(CHR$^5$)$_n$— where n is equal to 2, 3, 4, or 5, n preferably being equal to 3 or 4. R$^5$ represents either an H atom or a methyl, ethyl, propyl or butyl group. R$^5$ is preferably H. If R$^5$ is an alkyl group, then preferably only one $R^5$ in —(CHR$^5$)$_n$— is alkyl, the others then denoting H.

Furthermore, X may denote a —2—C$_6$H$_4$—(CH$_2$)$_m$— or a —2—C$_6$H$_{10}$—(CH$_2$)$_m$— group, and furthermore also a —(CH$_2$)$_m$—2—C$_6$H$_4$— or —(CH$_2$)$_m$—2—C$_6$H$_{10}$— group. In this case m is preferably 1.

Y in formula I denotes preferably —NR$^3$R$^4$, but also —PR$^3$R$^4$, —AsR$^3$R$^4$ or —SbR$^3$R$^4$. Y may also be a 5- or 6-membered heterocyclic ring (aromatic, or saturated or unsaturated aliphatic) containing one or more (e.g., 1, 2 or 3) atoms of group 5A, such as N, P or As. In particular, the following rings (1) to (5) are preferred:

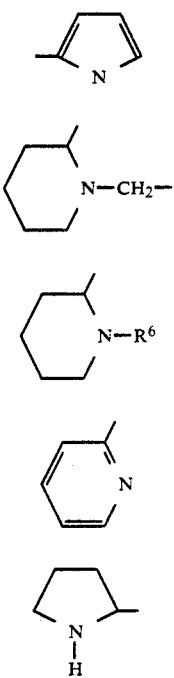

R$^6$ denoting H or an alkyl radical containing 1–8 carbon atoms.

The radicals R$^1$, R$^2$, R$^3$ and R$^4$ in formula I may in each case denote a straight-chain or branched alkyl group containing 1–8 carbon atoms, preferably containing 1–4 carbon atoms. They consequently denote preferably methyl, ethyl, propyl, butyl, isopropyl, sec-butyl, tert-butyl, but also pentyl, hexyl, heptyl, octyl, 2-methylpentyl, 3-methylpentyl or 2-octyl. The alkyl radicals may be partially or even completely fluorinated and may denote, for example, monofluoromethyl, trifluoromethyl, difluoroethyl, trifluoroethyl, pentafluoroethyl or trifluoropropyl.

If R$^1$, R$^2$, R$^3$ and/or R$^4$ denote a cycloalkyl or cycloalkenyl group, then they preferably represent cyclopentyl, cyclohexyl or cyclohexenyl. R$^1$ to R$^4$ may also be alkenyl groups containing 3–8 carbon atoms, i.e. propenyl, butenyl, pentenyl, hexenyl, heptenyl or allyl. If R$^1$ and/or R$^2$ and/or R$^3$ and/or R$^4$ denote(s) a phenyl group then the latter is preferably unsubstituted, but it may also be substituted. Since these substituents exert no substantial influence on the desired application, all substituents are permitted which have no disturbing influence on the decomposition reaction.

The following compounds may be regarded as exemplary representatives of compounds of formula I:
(2-dimethylaminobenzyl)dimethylindium
(3-dimethylaminopropyl)dimethylaluminum
(3-diethylaminopropyl)dimethylaluminum
(3-diethylaminopropyl)diisobutylaluminum
(3-diisopropylaminopropyl)dihexylaluminum
(4-N-methyl-N-isopropylaminobutyl)diethylaluminum
[3-(1-piperidyl)propyl]diethylaluminum
[2-(2-pyridyl)ethyl]dimethylaluminum
[3-(2-pyridyl)propyl]diisobutylaluminum.

The intramolecular stabilization, which is based on a bond between the metal atom and the particular heteroatom of group Y, which is separated from the metal by 2, 3, 4 or 5 carbon atoms, is essential for the novel use of the compounds of formula I. As a result of this intramolecular bond, the compounds of the formula I attain a significantly higher stability towards air and oxygen compared with the free metal alkyls. They are no longer spontaneously inflammable and can therefore be handled simply and without fairly considerable precautionary measures.

Some of the compounds of Formula I are known, but most are novel.

New compounds are, in particular, those of formula II

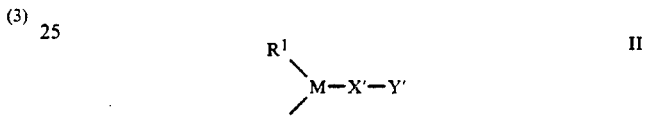

wherein

M denotes aluminum, indium or gallium,

X' denotes —2—C$_6$H$_4$—(CH$_2$)$_m$—, —(CH$_2$)$_m$—2—C$_6$H$_4$—, —2—C$_6$H$_{10}$—(CH$_2$)$_m$—, —(CH$_2$)$_m$—2—C$_6$H$_{10}$—, where m=1 or 2, Y' denotes —NR$^3$R$^4$, —PR$^3$R$^4$, —AsR$^3$R$^4$ or —SbR$^3$R$^4$ and R$^1$, R$^2$, in each case denote, independently of each other, R$^3$, R$^4$ H, a straight-chain or branched alkyl group containing 1–8 carbon atoms, which may be partially or completely fluorinated, a cycloalkyl, alkenyl or cycloalkenyl group containing in each case 3–8 carbon atoms or an unsubstituted or substituted phenyl group, with the proviso that R$^1$, R$^2$, R$^3$ and R$^4$ do not simultaneously denote methyl if M denotes indium, X' denotes —2—C$_6$H$_4$—CH$_2$— and Y' denotes —NR$^3$R$^4$.

At the same time, M preferably denotes gallium or indium. X' is preferably —2—C$_6$H$_4$—CH$_2$—, —CH$_2$—2—C$_6$H$_4$— or —2—C$_6$H$_{10}$—CH$_2$—. Y' preferably has the meaning of NR$^3$R$^4$. R$^1$, R$^2$, R$^3$ and R$^4$ have and meanings specified for formula I.

The compounds of the formula II include, for example, the following substances:
2-dimethylaminobenzyl (dimethyl)gallium
2-dimethylaminobenzyl (dimethyl)aluminum
2-diethylaminobenzyl(dimethyl)indium
2-dimethylaminobenzyl(diethyl)indium
2-diethylaminobenzyl(diethyl)gallium
2-diethylaminobenzyl(dimethyl)gallium
2-dimethylaminophenylmethyl(dimethyl)gallium
2-dimethylaminophenylmethyl(dimethyl)indium
2-dimethylaminophenylmethyl(dimethyl)gallium
2-dimethylaminophenylmethyl(dimethyl)aluminum
2-diethylaminocyclohexylmethyl(dimethyl)gallium
2-dipropylaminocyclohexylmethyl(dimethyl)aluminum
2-dimethylaminomethylcyclohexyl(dimethyl)indium.

The compounds of formula III are also new:

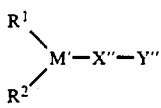

wherein
M' denotes gallium or indium,
X" denotes —$(CHR^5)_n$— where n=2, 3, 4, or 5,
$R^5$ in each case denotes H or an alkyl group containing 1-4 carbon atoms,
Y" denotes 5- or 6-membered heterocyclic ring, the heteroatom(s) originating from group 5A or —$NR^3R^4$, —$PR^3R^4$, $AsR^3R^4$ or —$SbR^3R^4$, and
$R^1$, $R^2$, in each case denote, independently of each $R^3$, $R^4$ other, H, a straight-chain or branched alkyl group containing 1-8 carbon atoms which may be partially or completely fluorinated, a cycloalkyl, alkenyl or cycloalkenyl group containing in each case 3-8 carbon atoms or an unsubstituted or substituted phenyl group.

At the same time, n in X" preferably denotes 3 or 4. Y" is preferably —$NR^3R^4$, but also —$PR^3R^4$ or —$AsR^3R^4$. If Y" is a heterocyclic compound containing atom(s) of group 5A, then rings containing N, P or As, but preferably the rings (1) to (5) specified for Y in formula I, are suitable. The meanings specified for formula I apply to $R^1$-$R^4$.

A number of compounds are listed below as exemplary representatives:
(3-dimethylaminopropyl)dimethylgallium
(3-dimethylaminopropyl)dimethylindium
(3-diethylaminopropyl)dimethylgallium
(3-diethylaminopropyl)dimethylindium
(3-diethylaminopropyl)diethylindium
(4-diethylaminobutyl)dimethylgallium
(4-diisopropylaminobutyl)dimethylindium
[2-(2-pyridyl)ethyl]dimethylindium
(4-N-methyl-N-isopropylaminobutyl)diethylgallium
(4-dimethylaminobutyl)diisopropylgallium
(3-dipropylaminopropyl)diethylgallium
(3-N-propyl-N-isopropylaminopropyl)diisobutylindium
(4-dimethylaminobutyl)diethylindium
(4-diethylaminobutyl)diethylgallium.

The compounds of the formulae I, II and III are outstandingly suitable for MOCVD epitaxy or for the MOCVD method since they decompose at fairly high temperatures to liberate the relevant metal. The are likewise suitable for the other methods of gas-phase deposition, such as photo-MOVP, laser CVD or MOMS.

The compounds of formulae I, II and III are prepared by methods which are known per se such as are described in the literature (for example, G. Bähr, P. Burba, Methoden der Organischen Chemie (Methods of Organic Chemistry), volume XIII/4, Georg Thieme Verlag, Stuttgart (1970)), specifically under reaction conditions which are known and are suitable for the reactions mentioned. At the same time, use may also be made of variants which are known per se but not mentioned here.

Those skilled in the art may obtain suitable methods of synthesis by routine methods from the prior art (for example, U.S. Pat. No. 3,154,528, or Jastrzebski et al, Organometallics 1982, 1, 1492, or Müller, Chem. Ber. 88, 251, 1765 (1955)).

Thus, compounds of the formulae I, II and III may be prepared, for example, by reacting metalalkyl chlorides with an alkali metal organic compound of the corresponding Lewis base or a Grignard compound in an inert solvent.

The reactions are preferably carried out in an inert solvent. Suitable solvents in this connection are all those which do not interfere with the reaction and do not intervene in the reaction process. The reaction temperatures essentially correspond to those which are known from the literature for the preparation of similar compounds.

In the novel method for the production of thin films or epitaxial layers on any desired substrate, use is made of the intramolecularly stabilized compounds of the formulae I, II and III as starting organometallic compounds in the gas-phase deposition processes known per se of organometallic compounds.

To produce compound semiconductors, one or more compounds of arsenic, antimony or phosphorus which are gaseous under the reaction conditions used are added during the deposition process in the decomposition chamber.

The layers produced by the novel methods may be used for the production of electronic and optoelectronic switching elements, compound semiconductors or lasers.

The deposition methods of this invention are fully conventional except for the use of the compounds of formula I and the concomitant advantages. For the conventional aspects, see, e.g. M. J. Ludowise in J. Appl. Phys. 58 (8), 1985, 31 or J. B. Webb in Appl. Phys. Lett. 47 (8), 1985, 831.

Typically, for this invention, decomposition temperatures will be 400°-1000° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

In the following examples, M.p. denotes melting point and B.p. denotes boiling point.

EXAMPLES

Example 1

12 g (89 mmol) of dimethylgallium chloride are made ready for use in 300 ml of pentane and cooled to −78°. 8.3 g (89 mmol) of dimethylaminopropyllithium are added thereto as a solid. The solution is allowed to come to room temperature and is stirred for a further 24 hours. The lithium chloride precipitated is separated off, the solvent is removed and the residue is distilled in vacuo. Dimethylaminopropyl(dimethyl)gallium is obtained as a white solid with a B.p. of 65°/10 mbar.

Example 2

3.6 g (30 mmol) of diethylaminopropyllithium dissolved in 100 ml of pentane are added to a solution of 4 g (30 mmol) of dimethylgallium chloride in 50 ml of pentane at −78°. The solution is allowed to come to room temperature and is stirred for a further 24 hours. The working up is carried out analogously to Example 1. Instead of the distillation, a sublimation is carried out. Diethylaminopropyl(dimethyl)gallium with an M.p. of 43°-45° is obtained.

Example 3

4.3 g (30 mmol) of o-lithium-N,N-dimethylbenzylamine are added to a solution of 4 g (30 mmol) of dimethylgallium chloride in 150 ml of pentane at −78°. Working up is carried out analogously to Example 1 with sublimation as the purification step. 1,2-Dimethylaminobenzyl(dimethyl)gallium with an M.p. of 29°-31° is obtained.

Example 4

Dimethylaminopropyl(dimethyl)aluminum with M.p. of 52° is obtained analogously to Example 1 from dimethylaluminium chloride and dimethylaminopropyllithium.

Preparation Example 5

5.47 g (30 mmol) of (3-dimethylarsinopropyl)chloride are added to 1.44 g (60 mmol) of magnesium chips in 100 ml of diethylether at 20° C., and then the mixture is heated under reflux for two hours. The solution is allowed to come to room temperature, 4.0 g (30 mmol) of dimethylgallium chloride in 50 ml of diethylether are added, and the solution is refluxed again for two hours. The working up is carried out analogously to Example 1. (3-Dimethylarsinopropyl)-dimethylgallium is obtained as a clear liquid with a B. p. of 86° C./0.01 mbar.

Preparation Example 6

Analogously to Example 3, 1,2-diethylphosphinobenzyl(dimethyl)indium with a B. p. of 88° C./0.3 mbar is obtained by reacting o-lithium-diethylbenzylphosphine with dimethylindium chloride. The working up is carried out analogously to Example 1.

B. Use for Producing Thin Films

Example 1

Dimethylaminopropyl(dimethyl)gallium (prepared according to Example 1) is filled into the "bubbler" and connected to the gas supply of the inert gas and the decomposition chamber. Depending on the partial vapor pressure of the reagent in the reactor, decomposition takes places with the deposition of gallium at temperatures from approximately 700° C.

Example 2

Diethylaminopropyl(dimethyl)indium (which can be prepared analogously to Example 1) is filled into the "bubbler", converted to the vapor state by means of the carrier gas, and conveyed to the decomposition chamber. A phosphine is additionally passed into the decomposition chamber. The gaseous substances decompose in the decomposition chamber at a temperature of approximately 650° and deposit on the substrate as an InP coating.

Example 3

1,2-Diethylphosphinobenzyl(dimethyl)indium was decomposed with $PH_3$ in a MOCVD apparatus under normal pressure. The growth temperature ranged between 580° C. and 660° C.; an epitaxial InP-layer was obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for gas-phase deposition of a metal compound containing Al, In or Ga on a substrate, the improvement wherein a source of Al, In or Ga for the deposition process is an organometallic compound of the formula

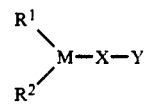

wherein
M is Al, In or Ga;
X is $-(CHR^5)_n-$ where n=2, 3, 4 or 5, $-2-C_6H_4-(CH_2)_m-$, $-(CH_2)_m-$, $-(CH_2)_m-2-C_6H_4-$, $-2-C_6H_{10}-(CH_2)_m-$, or $-(CH_2)_m-2-C_6H_{10}-$ where m=1 or 2;
$R^5$ is H or alkyl containing 1-4 carbon atoms;
Y is $-PR^3R^4$, $-AsR^3R^4$, $SbR^3R^4$, or a 5- or 6-membered heterocyclic ring where the heteroatoms are from group 5A; and
$R^1$, $R^2$, $R^3$ and $R^4$ are each independently H, straight-chain or branched alkyl containing 1-8 carbon atoms, partially or completely fluorinated straight-chain or branched alkyl containing 1-8 carbon atoms, cycloalkyl, alkenyl or cycloalkenyl containing in each case 3-8 carbon atoms, unsubstituted phenyl or substituted phenyl.

2. A process according to claim 1, wherein an epitaxial layer is deposited.

3. A process according to claim 1, wherein a thin film is deposited.

4. A process according to claim 1, wherein X is $-(CHR^5)_n-$ and n is 3 or 4.

5. A process according to claim 1, wherein X is $-(CHR^5)_n-$, one $R^5$ group is alkyl, and the remaining $R^5$ groups are H.

6. A process according to claim 1, wherein X is $-2-C_6H_4-CH_2-$, $-2-C_6H_{10}-CH_2-$, $-CH_2-2-C_6H_4-$, or $-CH_2-2-C_6H_{10}$.

7. A process according to claim 1, wherein $R^1$ to $R^4$ are each independently straight-chain or branched alkyl containing 1-4 carbon atoms, partially or completely fluorinated straight-chain or branched alkyl containing 1-4 carbon atoms, propenyl, butenyl, pentenyl, hexenyl, heptenyl, allyl, cyclopentyl, cyclohexyl, cyclohexenyl, or unsubstituted phenyl.

* * * * *